Figure 1:
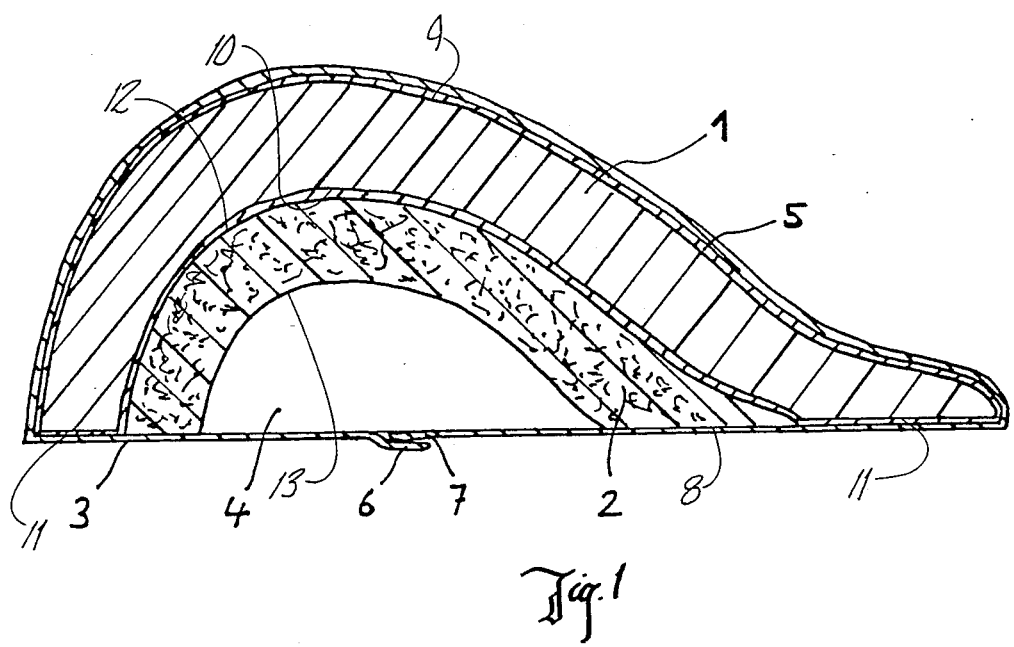

United States Patent [19]

Eberl et al.

[11] Patent Number: 4,795,464
[45] Date of Patent: * Jan. 3, 1989

[54] ARTIFICIAL BREAST

[75] Inventors: Tertulin Eberl, Nonnenwaldstrasse 25, D-8122 Penzberg, Fed. Rep. of Germany; Georg Weber-Unger, Kufstein, Austria

[73] Assignees: Tertulin Eberl, Penzberg, Fed. Rep. of Germany; Anita-Spezialmiederfabrik Dr. Helbig Gesellschaft m.b.H. & Co. KG, Kufstein, Austria

[*] Notice: The portion of the term of this patent subsequent to Jul. 21, 2004 has been disclaimed.

[21] Appl. No.: 20,485

[22] Filed: Mar. 2, 1987

Related U.S. Application Data

[63] Continuation-in-part of Ser. No. 794,702, Nov. 4, 1985, Pat. No. 4,681,587, which is a continuation of Ser. No. 600,483, Apr. 16, 1984, abandoned.

[30] Foreign Application Priority Data

Feb. 9, 1987 [DE] Fed. Rep. of Germany ... 8701925[U]

[51] Int. Cl.$^4$ .............................................. A61F 2/12
[52] U.S. Cl. ...................................................... 623/8
[58] Field of Search ............................................ 623/7, 8

[56] References Cited

U.S. PATENT DOCUMENTS 3,706,104 12/1972 Dehlin et al. ..................... 623/7
4,681,587 7/1982 Eberl et al. ....................... 623/7

FOREIGN PATENT DOCUMENTS 0005275 11/1979 European Pat. Off. ............ 623/8
0933052 7/1963 United Kingdom ................ 623/8

Primary Examiner—Richard J. Apley
Assistant Examiner—David J. Isabella
Attorney, Agent, or Firm—Zarley, McKee, Thomte, Voorhees & Sease

[57] ABSTRACT

The artificial breast prosthesis of the present invention comprises an outer shell of silicone material having a concave cavity formed at its rear surface. Nested within this concave cavity is a plastic foam shell which in turn has a concave cavity at its rear surface. The outer silicone shell and the foam body member nested within the outer shell are both enclosed within a fabric pocket having a rear slit therein for permitting removal of the silicone and foam body members.

12 Claims, 1 Drawing Sheet

U.S. Patent
Jan. 3, 1989
4,795,464

180# ARTIFICIAL BREAST

This is a continuation-in-part of application Ser. No. 794,702, filed Nov. 4, 1985, now U.S. Pat. No. 4,681,587 which a continuation of application Ser. No. 600,483, filed Apr. 16, 1984, and now abandoned.

BACKGROUND OF THE INVENTION

The invention relates to an artificial breast according to the preamble of claim 1.

Such a breast prosthesis is known from EP-A-0 125 400. In this artificial breast, the rear side of the pad or cushion body is planar and flush throughout with the plane rear edge face of the prosthestic body surrounding the depression or hollow of the prosthetic body. Consequently, the rear side of the fabric pocket surrounding the prosthetic body and the cushion body bears throughout on the rear side of the cushion body and the rear end face of the prosthetic body.

With such a prosthesis, at the remaining breast tissue on which it bears with its rear side skin irritations may arise which are due to the prosthesis preventing ventilation of the remaining breast tissue and the cushion body pressing with its entire rear area on the remaining breast tissue, this application pressure being the more unpleasant and irritating for the wearer the greater the amount of projecting breast tissue which has been left.

The problem underlying the invention is to further develop the artificial breast according to the preamble such that the rear side of the prosthesis bears more gently on the body of the prosthesis wearer, air is allowed to reach the remaining breast tissue and the adaptability of the rear side of the artificial breast to projecting remaining tissue is increased, the mobility and elasticity of the overall prosthesis being retained.

This problem is solved according to the invention with the features of the characterizing clause of the claim.

The artificial breast according to the invention has the advantage that the engagement area of the cushion body on the body of the prosthesis wearer is considerably reduced, that the rear side of the prosthesis can adapt itself to projecting unremoved breast tissue without pressure concentrations and that the prosthesis due to the resilient supporting on the body has an improved oscillation behaviour which makes it resemble still more a natural breast. Furthermore, the artificial breast according to the invention has the advantage that the unremoved breast tissue is regularly ventilated, and air exchange at the rear side of the prosthesis being promoted not only by the greatly reduced engagement area of the cushion body but also by the pump effect of the elastic rear side of the fabric envelope occurring under dynamic load. However, such an elastic textile fabric at the rear side of the fabric sheath or envelope is known in practice.

An example of the embodiment is illustrated in the attached drawing and will be described in detail hereinafter.

The drawing shows a cross-section of a breast prosthesis according to the invention.

As apparent from the drawing, the artificial breast consists of a prosthetic body (1), a cushion body (2), and a fabric pocket (3) surrounding the prosthetic body and the cushion body. The prosthetic body (1) comprises silicone rubber which is a gel-like mass which in its consistency and specific weight corresponds to the consistency and the specific weight of natural mammary tissue. The prosthetic body (1) is surrounded by a very thin elastically stretchable tear-resistant polyurethane foil or skin (5). The front side (9) of the prosthetic body (1) has a form corresponding to the natural breast. On the rear side (10) of the prosthetic body (1), there is a depression which follows the contour of the front side. Extending circumferentially around the depression formed by rear surface (10) is an annular edge (11) of body (1) which is presented towards the body of the wearer of the prosthesis. Thus, as a whole, the prosthetic body (1) has a dish form. In the depression of the prosthetic body (1), a cushion body (2) of foamed plastic is disposed which has a considerably lower specific weight than the silicone rubber material of the prosthetic body (1). Cushion body (2) includes a front surface (12) which conforms substantially to rear surface (10) of body (1) and provides support thereto. Cushion body (2) has a rear concave surface (13) which conforms substantially to its front surface (12) and to the front and rear surfaces (9, 10) of body (1).

The depression or hollow of the prosthetic body (1) reduces the total weight of the artificial breast considerably and the cushion body (2), whose weight is negligibly small compared with that of the prosthetic body (1), exerts a supporting action on the prosthetic body (1) so that the latter cannot collapse.

The cushion body (2) is detachably held in the depression of the prosthetic body (1) by the fabric pocket (3) surrounding the prosthetic body (1) on the front side and the cushion body (2) on the rear side. It is known in practice to make the rear side of the fabric pocket from knitted textile cloth consisting for example, of 95% cotton. The fabric pocket (3) has at its rear side a slit-shaped opening which is closed by two overlapping ends (6,7) of the pocket rear side. By pulling the ends (6 and 7) apart, the slit-shaped opening is widened so that the cushion body (2) and the prosthetic body (1) can be removed individually or together from the fabric pocket (3) and reintroduced into the latter.

The cushion body (2) on its rear side (13) forms a depression (4) and substantially follows the contour of the front side (12) of the cushion body (2). Extending circumferentially around depression (4) is an annular edge (8) of body (2) which is presented toward the body of the wearer and which is in approximately the same plane as the annular edge (11) of body (1). The depression (4) is of such magnitude that the rear planar edge face (8) of the cushion body (2) which surrounds the depression (4) makes up only about one-third of the total rear planar area of the cushion body (2) projected into a plane. Furthermore, the depression (4) is located at the approximate center of the rear of the prosthesis so that it will be located adjacent any remaining breast tissue of the wearer.

The rear side of the fabric pocket (3) spans depression (4) in rearward spaced relation from rear surface (13) of body (2). Fabric pocket (3) is elastic and is therefore easy to press, with elastic deformation, into the depression (4), then bearing partially or entirely on the surface of the depression (4). Remaining projecting breast tissue can be accommodated without appreciable counter pressure in the depression (4) of the cushion body (2). Furthermore, due to the depression (4) regular ventilation of the remaining breast tissue is possible. The portion of the rear side of the fabric pocket (3) extending over the depression (4) permits resilient support of the entire artificial breast on the body of the wearer. The elasticity and mobility of the entire prosthesis is not impaired by the depression (4).

The fact that the body (1) is comprised of silicone material having a consistency and specific weight of the natural breast tissue, and the fact that the body member 2 is formed of a material lighter in specific weight of the body, and the further fact of the depression 13, permits the present invention to accomplish several results. First, the overall weight of the device is reduced by virtue of the fact that the major volume of the prosthesis is occupied by the backing member (2) which is light in specific weight and by the depression (4). At the same time, the outer surface of the prosthesis formed by the silicone material (1) has the same feel and consistency of natural breast tissue.

The backing member (2) provides the function of supporting the outer body (1) while at the same time reducing substantially the total weight of the prosthesis. If the prosthesis were solid silicone, it would be too heavy and would place undue stress on the brassiere in which it is inserted and the straps supporting the brassiere. Because the body (1) is formed into a silicone shell to reduce its weight, it tends to collapse and be unusable unless it is otherwise supported. Therefore, the low density backing member (2) supports the body while permitting a substantial reduction in weight. Without backing member (2), the outer body member would collapse and be unusable.

Furthermore, the silicone material of the body can be a source of irritation when it is presented towards the scar tissue of the person having the mastectomy. The body member (2) is made of a foam material, and provides less of a source of irritation. The open space provided by depression (4) minimizes the irritation at the center of the prosthesis where the location of projecting scar tissue is most likely to be located. Thus, the present invention minimizes irritation to the wearer by having the rearward opening of depression (4) be substantially free of the silicone of the body (1) so as to minimize interference of the silicone of the body with the scar tissue and so as to expose a substantial portion of the center of the prosthesis rearwardly towards the scar tissue of the person.

Thus, it can be seen that the device accomplishes at least all of its stated objectives.

What is claimed is:

1. Artificial breast to be worn on the body of a person who has had a mastectomy, said artificial breast comprising a dish-shaped prosthetic body of silicone rubber resembling in its consistency and specific weight the natural breast tissue and which is covered with a polyurethane sheet, a front side adapted to the form of the natural breast and a rear side which forms a depression and which follows the contour of the front side, and a cushion body which is disposed in the depression, has a front side following the contour of the rear side of the prosthetic body and is detachably held in the depression by a fabric pocket which surrounds the prosthetic body on the front side and the cushion body on the rear side and which on its rear side has a slit-like opening which is closable by two overlapping ends of the rear side of the fabric pocket and through which the cushion body can be introduced into the depression of the prosthetic body and removed therefrom, characterized in that the rear side of the cushion body (2) forms a depression (4) which substantially follows the contour of the front side of the cushion body and that the rear side of the fabric pocket (3) comprises an elastic textile fabric, extends spaced from the bottom of the depression (4) of the cushion body (2) and can be pressed with elastic deformation into the depression (4) of the cushion body (2), the cushion body (2) being comprised of a foam plastic and having a specific weight which is lighter in specific weight than the prosthetic body (1), the foam plastic of cushion body (2) having the characteristic of providing less irritation to the wearer's body than the silicone rubber of the prosthetic body (1).

2. Artificial breast according to claim 1, characterized in that the cushion body (2) comprises a rear support face which makes up substantially a third of the total rear end face of the cushion body projected onto a plane.

3. An artificial breast according to claim 1 characterized in that said prosthetic body (1) includes an annular edge (11) extending circumferentially around said depression (10) of said prosthetic body (1) and facing rearwardly; said cushion body (2) including an annular edge (8) extending circumferentially around said depression (4) of said cushion (2) and facing rearwardly in approximately the same plane as said annular edge (11) of said prosthetic body.

4. An artificial breast according to claim 3 characterized in that said annular edge (8) of said cushion body (2) is completely located radially inwardly from said annular edge (11) of said prosthetic body (1).

5. An artificial breast according to claim 1 wherein said cushion body (2) is separable from and removable from said depression (10) of said prosthetic body (1) through said slit-like opening (6,7) of said fabric pocket (3).

6. An artificial breast according to claim 3 wherein said fabric pocket completely surrounds said prosthetic body (1), said cushion body (2), and said depression (4) of said cushion body (4); said rear side of said fabric pocket extending in approximately the same plane as said annular edges (8, 11) of said prosthetic body (1) and said cushion body (2), respectively.

7. A mastoprosthesis for wearing within a brassiere by a person having mastectomy scar tissue located rearwardly of said brassiere, said mastoprosthesis comprising:

a body comprising as inner solid core of a soft silicone material resembling in consistency and specific weight the natural breast tissue, said body having a front surface which is contoured to conform to the shape of a female breast and a rear surface defining a body depression;

a cushion member inserted within said body depression and being comprised of a soft resilient material which is lighter in specific weight than aid body, said cushion member having a front surface facing and conforming substantially to said rear surface of said body and having a rear surface forming a cushion member depression;

a pocket member completely surrounding said body and said cushion member, said pocket member having a front wall covering said front surface of said body and having a rear wall spanning and covering said cushion member depression so as to define an enclosed cavity therein, said rear wall being comprises of a flexible material capable of elastic deformation into said cushion member depression.

8. A mastoprosthesis according to claim 7 wherein said body includes an annular rearwardly facing edge defining the rear margin of said body depression, said cushion member being positioned completely within said body depression and completely inside said annular rearwardly facing edge of said body.

9. A mastoprosthesis according to claim 7 wherein said rear wall of said pocket member is directly exposed to said enclosed cavity.

10. A mastoprosthesis according to claim 7 wherein said cushion member is removable from said body depression.

11. A mastoprosthesis according to claim 10 wherein said body and said cushion member are removable from said pocket member.

12. A mastoprosthesis according to claim 11 wherein said rear wall of said pocket member includes two overlying flap portions which are adapted to be separated from one another so as to define an opening through which said body and said cushion member can be removed from said pocket member.

* * * * *